(12) United States Patent
Heston

(10) Patent No.: US 8,900,266 B2
(45) Date of Patent: Dec. 2, 2014

(54) TOURNIQUET CUFF WITH A TIGHTNESS INDICATOR

(75) Inventor: Brian K. Heston, Dover, OH (US)

(73) Assignee: Zimmer Surgical, Inc., Dover, OH (US)

( * ) Notice: Subject to any disclaimer, the term of this patent is extended or adjusted under 35 U.S.C. 154(b) by 868 days.

(21) Appl. No.: 12/185,270

(22) Filed: Aug. 4, 2008

(65) Prior Publication Data

US 2009/0062843 A1 Mar. 5, 2009

Related U.S. Application Data

(60) Provisional application No. 60/968,652, filed on Aug. 29, 2007.

(51) Int. Cl.
*A61B 17/00* (2006.01)
*A61B 17/135* (2006.01)
*A61B 19/00* (2006.01)

(52) U.S. Cl.
CPC ....... *A61B 17/135* (2013.01); *A61B 2019/4836* (2013.01); *A61B 2017/0023* (2013.01); *A61B 19/30* (2013.01)
USPC ....................................................... 606/203

(58) Field of Classification Search
CPC .. A61B 17/12; A61B 17/1325; A61B 17/135; A61B 17/132; A61B 17/1322; A61B 17/1355; A61B 5/02233; A61B 17/1327; A61H 9/0078; A61H 2201/5074; A61H 39/04; A61H 2205/027; A61H 2205/067
USPC .............. 606/201–204, 153; 24/18, 300, 301; 600/37
See application file for complete search history.

(56) References Cited

U.S. PATENT DOCUMENTS

| | | | | |
|---|---|---|---|---|
| 1,424,329 A | * | 8/1922 | Walsh | 2/323 |
| 2,068,173 A | * | 1/1937 | Galves | 600/41 |
| 2,258,720 A | * | 10/1941 | Saighman | 606/203 |
| 2,302,843 A | * | 11/1942 | Dorion | 450/115 |
| 3,033,199 A | * | 5/1962 | Jacobs | 128/201.25 |
| 3,086,529 A | * | 4/1963 | Munz et al. | 606/203 |
| 3,173,420 A | * | 3/1965 | Mazzoni et al. | 450/54 |
| 3,279,459 A | | 10/1966 | Schenker | |
| 3,390,680 A | * | 7/1968 | Marcum | 606/203 |

(Continued)

FOREIGN PATENT DOCUMENTS

WO 97/39709 A1 10/1997

OTHER PUBLICATIONS

International Search Report, PCT/US2008/072116, Date of Mailing: Nov. 11, 2008.

(Continued)

*Primary Examiner* — Darwin Erezo
*Assistant Examiner* — Amy Shipley
(74) *Attorney, Agent, or Firm* — Seager, Tufte & Wickhem, LLC

(57) ABSTRACT

A tourniquet cuff has a body configured for being wrapped around a limb. The body has an unpressurized state and a pressurized state. A securing portion on the body is releasably engageable to the body. The cuff also has an indicator that operates in response to movement of the securing portion for locating where the securing portion engages the body in order to apply a predetermined amount of force sufficient to secure the body to a limb without causing significant venous occlusion at the limb when the body is in the unpressurized stated.

21 Claims, 3 Drawing Sheets

(56) References Cited

U.S. PATENT DOCUMENTS

| | | | |
|---|---|---|---|
| 4,605,005 A * | 8/1986 | Sheehan | 606/216 |
| 4,605,010 A * | 8/1986 | McEwen | 600/499 |
| 4,635,635 A | 1/1987 | Robinette-Lehman | |
| 5,201,758 A * | 4/1993 | Glover | 606/202 |
| 5,387,183 A * | 2/1995 | Jones | 602/19 |
| D362,068 S | 9/1995 | Baker et al. | |
| 5,454,831 A * | 10/1995 | McEwen | 606/202 |
| 5,514,155 A * | 5/1996 | Daneshvar | 606/201 |
| 5,591,122 A * | 1/1997 | Yewer, Jr. | 602/19 |
| 5,649,954 A * | 7/1997 | McEwen | 606/202 |
| 5,702,042 A * | 12/1997 | Peacock | 224/662 |
| 5,904,145 A | 5/1999 | Reid | |
| 5,916,183 A | 6/1999 | Reid | |
| 6,245,024 B1 * | 6/2001 | Montagnino et al. | 600/499 |
| 6,361,548 B1 * | 3/2002 | McEwen | 606/201 |
| 6,506,206 B1 * | 1/2003 | Guzman et al. | 606/203 |
| 6,682,547 B2 * | 1/2004 | McEwen et al. | 606/202 |
| 6,746,470 B2 * | 6/2004 | McEwen et al. | 606/202 |
| 7,384,425 B2 * | 6/2008 | McEwen | 606/201 |
| 7,892,253 B2 * | 2/2011 | Esposito et al. | 606/203 |
| 7,981,135 B2 * | 7/2011 | Thorpe | 606/203 |
| 8,343,182 B2 * | 1/2013 | Kirkham | 606/203 |
| 8,481,803 B2 * | 7/2013 | Wada et al. | 602/53 |
| 2002/0188315 A1 * | 12/2002 | Guzman et al. | 606/203 |
| 2003/0036771 A1 * | 2/2003 | McEwen et al. | 606/202 |
| 2003/0144596 A1 * | 7/2003 | Tsubata | 600/500 |
| 2003/0167070 A1 * | 9/2003 | McEwen et al. | 606/203 |
| 2003/0199922 A1 * | 10/2003 | Buckman | 606/202 |
| 2006/0190026 A1 | 8/2006 | Sanders | |
| 2008/0312682 A1 * | 12/2008 | Shams et al. | 606/203 |
| 2011/0087264 A1 * | 4/2011 | Esposito | 606/203 |
| 2012/0071917 A1 * | 3/2012 | McDonald et al. | 606/203 |
| 2012/0221044 A1 * | 8/2012 | Archibald et al. | 606/214 |
| 2013/0104288 A1 * | 5/2013 | Schlottau et al. | 2/209.13 |

OTHER PUBLICATIONS

Zimmer, Inc., Zimmer A.T.S. Reusable Cuffs, Low Profile High Performance, Brochure, 2003, 2006, 4 pages U.S.A.

Zimmer, Inc., Zimmer A.T.S. Disposable Cuffs, Low Profile High Performance, Brochure, 2003, 2006, 4 pages U.S.A.

Zimmer, Inc., Zimmer A.T.S. Contour Cuffs, Versatility and flexibility for both surgeon and patient, Brochure, 2007, 4 pages U.S.A.

Healthstream, Tourniquet Safety Study Guide for Nurses, Brochure, 2005, title pp. 1-2 and pp. 12, 18, U.S.A.

* cited by examiner

TOURNIQUET CUFF WITH A TIGHTNESS INDICATOR

CROSS-REFERENCE TO RELATED APPLICATIONS

This application claims the benefit of U.S. Provisional Application No. 60/968,652, filed Aug. 29, 2007, the contents of which are hereby incorporated by reference.

FIELD OF THE INVENTION

The present invention is directed to tourniquet cuffs that provide arterial and venous occlusion in the limb of a living being and, more particularly, to tourniquet cuffs with structure to indicate the proper application of the tourniquet cuff on the limb.

BACKGROUND OF THE INVENTION

Tourniquet cuffs are wrapped around the limb of a living being in order to keep blood out of the limb and/or to keep local anesthesia from escaping the limb. The cuffs are used for many different medical procedures performed on the limb such as orthopaedic surgeries to name one example. The conventional inflatable tourniquet cuffs are snuggly wrapped around the limb and secured by pressing a hook or loop type material surface such as VELCRO® on the free end of the cuff to a mating hook-loop type material surface along the body of the cuff. Inflatable cuffs have at least one fluid-tight bladder and one or more ports that extend from the bladder and out of the cuff. The ports are connected to tubes that are in turn connected to an air-supplying tourniquet machine. The air volume and pressure for inflating the cuff is then controlled at the tourniquet machine. The inflated cuff applies a force against the limb that is sufficient to occlude the arteries and veins extending through the limb to stop arterial blood flow to the limb and venous blood flow and anesthesia from flowing out of the limb.

When the cuff is first wrapped around the limb while the cuff is deflated, ideally the cuff should be secured so that the cuff is not too loose and not too tight. A cuff that is properly tightened on the limb will form a defined cylinder with spiraling layers. A cuff that is too loose, however, may "telescope" out of the cylindrical shape during use and along the patient's limb. This can cause a partial or total loss of occlusion of the arteries and veins.

On the other hand, a cuff that is too tight can cause venous occlusion even though the cuff is not inflated. Pre-surgery, venous occlusion can cause poor exsanguination such that a sufficient amount of blood cannot exit the limb due to the tight cuff. This can occur while using gravity exsanguination where the limb is elevated for a particular amount of time and/or while using tensors such as wraps or other elastic bandages used to squeeze the blood out of the limb.

Post-surgery, venous occlusion by a deflated cuff can form a venous tourniquet which means that the blood engorges the limb and pools in the limb because the veins are partially or fully occluded while the arteries are still bringing blood to the limb. This may cause a dangerous deep vein thrombosis (DVT) otherwise known as a blood clot. This can occur when a surgical team deflates the cuff but leaves the cuff applied to the limb while the surgical team performs other final procedures such as closing the wound, placing drains or catheters in or near the surgical site or checking range of motion of the implant. The surgical team may not notice that the cuff on the limb is too tight and is causing a venous tourniquet because the cuff applied on the limb is often covered by surgical drapes, bandages, distal seals and/or soft tissue protection layers used between the cuff and the limb which may extend beyond the cuff on the limb such as stockinettes, sleeves, cotton cast padding, or sheet padding.

A "1-2-3 finger" test or rule is known for determining if the deflated cuff was wrapped around the limb with the correct amount of tightness or pressure. For this rule, after the cuff is wrapped around the limb, the fit is checked by attempting to put one finger between the limb and the applied cuff. If one finger does not "fit", or is too tight, the cuff is applied too tight. If two fingers fit comfortably between the cuff and the limb but not too tightly, the cuff is applied properly. If three fingers fit between the cuff and the limb, the cuff is too loose. However, a more objective way is desired for determining whether or not a tourniquet is applied to a limb with the proper amount of force.

DETAILED DESCRIPTION OF THE PREFERRED EMBODIMENTS

Figure 1:
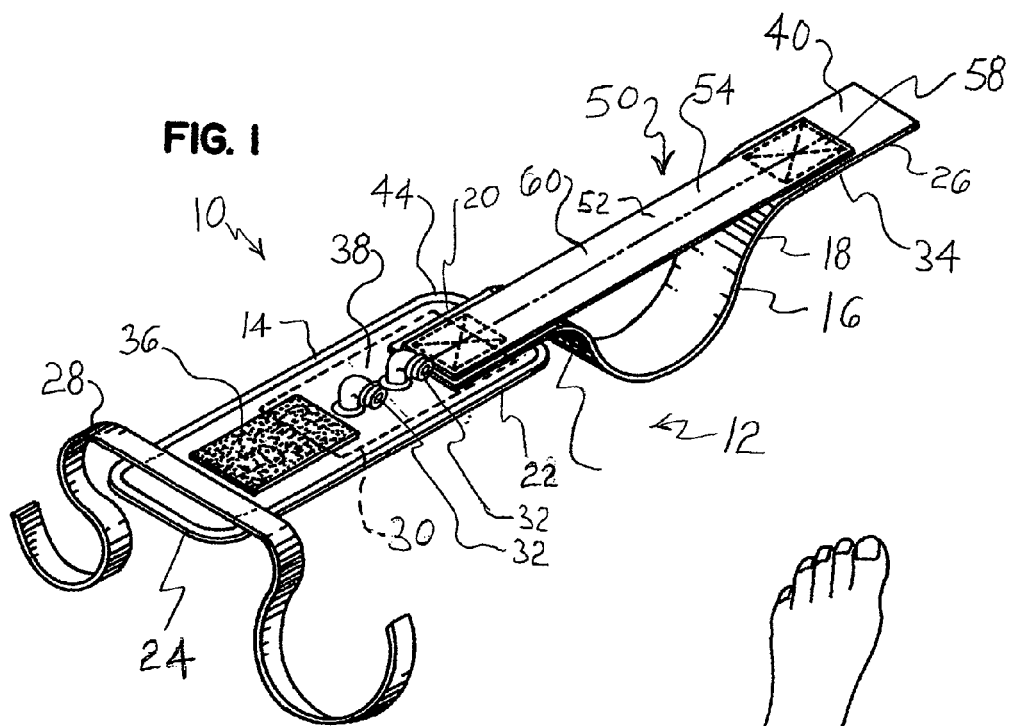
FIG. 1 is a front perspective view of a tourniquet cuff in accordance with the present invention.
Figure 2:
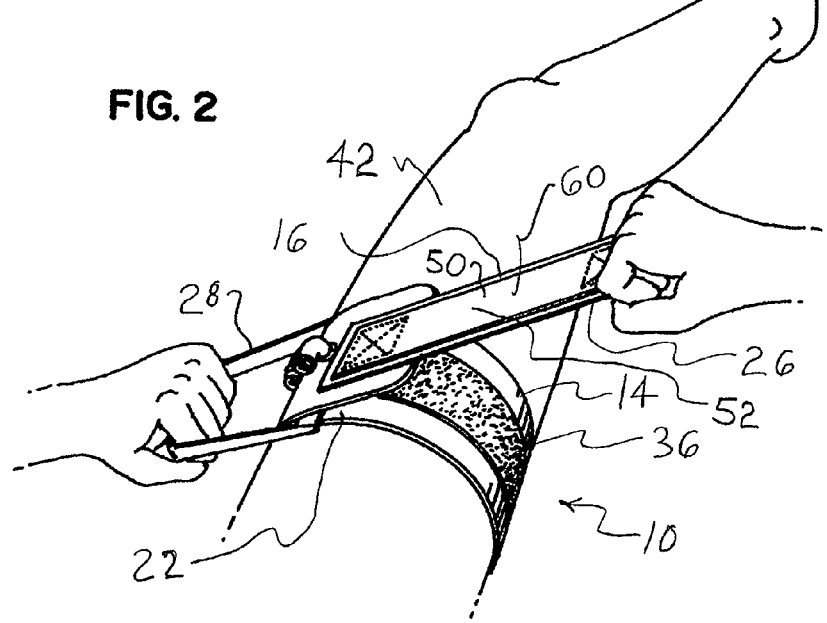
FIG. 2 is perspective view of the tourniquet cuff of FIG. 1 being applied to the limb of a living being.
Figure 3:
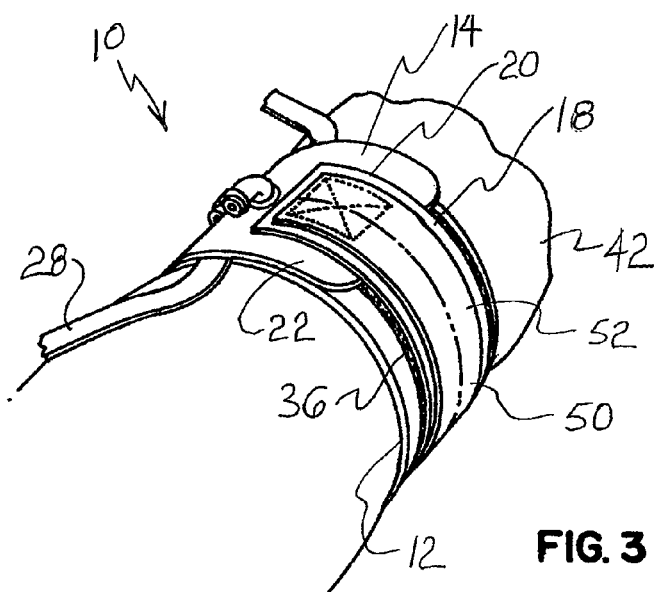
FIG. 3 is a perspective view of the tourniquet cuff of FIG. 1 shown fully secured to the limb in accordance with the present invention.

Referring to FIGS. 1-3, an inflatable tourniquet cuff 10 has a body 12 with a main member 14 and a securing portion 16 that includes a securing strap 18. The strap 18 has an attachment end portion 20 connected to an end portion 22 of the main member 14 at an intermediate portion 44 of the body 12. The body 12 has a proximal end portion 24 formed by the main member 14 and that is placed against a limb 42 for a medical procedure on the limb. A distal end portion 26 of the body 12 is formed by the securing strap 18 while a grasping ribbon 28 extends transversely along the proximal end portion 22 of the main member 14. The main member 14 also has one or more fluid-tight bladders, bags, or containers 30 (shown in dashed line) with one or more ports 32 for connection to a tourniquet machine that controls the air supply and pressure from and to the bladder 30 in order to pressurize and unpressurize the tourniquet cuff 10.

In one form, the main member 14 includes outer layers of woven nylon covering the bladder 30 and other inner, polymeric stiffening and/or protection layers. The securing strap 18 is secured to the end portion 22 of the main member 14 by adhesion, sewing, and/or any other suitable connection method. The securing strap 18 is also made of woven nylon or other polymeric material with a hook-type material on a back side 34 that faces the limb 42. The main member 14 has a patch 36 of loop-type material on the front side 38 of the main member 14 facing away from the limb. So configured, when the cuff 10 is wrapped around the limb, any part of the back side 34 of the securing strap 18 can be engaged to the patch 38 for securing the cuff to the limb. It will be appreciated, however, that the location of the engagement material on the securing strap or portion 18 is not limited to any one configuration. Thus, the hook and loop material locations may be reversed than that described above, and/or may be limited to certain parts of the securing strap 18 whether just on the back side 34 of the strap 18 or additionally on the front side 40 of the strap 18. The hook or loop-type material may also be limited to only certain portions of the securing strap 18 rather than extending the entire length of the strap.

The cuff 10 also has an indicator 50 that operates in response to movement of the securing portion 16 for locating where the securing portion 16 engages the body 12 in order to apply a predetermined amount of force sufficient to snugly secure the body 12 to the limb 24 without causing significant venous occlusion at the limb when the body is in the unpressurized state. The indicator 50 includes at least one resilient portion or resiliently extendable portion 52. The resilient portion 52 has a natural bias against extension and is attached to the body 12 so that the resilient portion is stretched or extends against the natural bias as the securing portion 52 is wrapped around the limb 24 for securement to the body.

More specifically, the resilient portion 52 includes an elastic strip 54, and as indicated by the phantom line, the indicator 50 may include a plurality of generally parallel resilient portions 52. The resilient portion 52 has a first end portion 56 connected to the end portion 22 of the main member 14 located at the intermediate portion 44 of the body 12. A second distal end portion 58 of the resilient portion 52 is connected to the distal end portion 26 of the body 12 and on the securing strap 18. The first and second end portions 56 and 58 of the resilient portion 52 are connected to the front face 40 of the securing strap 18 by adhesive, stitching (whether or not the same stitching holding the securing strap 18 to the main member 14), or other connection devices. Since the resilient portion 52 is attached to the body 12 at its end portions 56 and 58, an intermediate section 60 of the resilient portion and between the end portions is free to move away from the securing strap 18 when the resilient portion 52 has its natural length and the securing strap 18 is in a slackened state (as shown in FIG. 1). The intermediate section 60 generally extends along and in contact with the securing strap 18 when the securing strap is in a taut state and the resilient portion 52 is disposed in a predetermined, fully extended length or state (as shown in FIG. 2). The resilient portion 52 maybe made of expandable polymeric materials, whether woven or non-woven, such as latex-free lycra spandex or other polyurethane fiber materials although latex based fibers could be used.

To apply the cuff 10 to the limb 42, the body 12 is snugly wrapped around the limb forming a cylindrical shape of one or more layers around the limb. In one form, the user then holds the grasping ribbons 28 with one hand while pulling the securing strap 18 with the other hand as shown in FIG. 2. This extends the resilient portion 52 against its natural bias and absorbs forces that would have otherwise been applied directly to the main member 14 which could over-tighten the main member on the limb 42. In one form, the resilient portion 52 is extended into its fully extended length (or other predetermined extended state) when the securing strap 18 is pulled generally taut and the resilient portion 52 cannot be extended farther. In this orientation, the resilient portion 52, along with the tension applied by the user, applies a tensile force that is sufficient to hold the body 12 snugly on the limb 42 without significantly restricting blood flow out of the limb while the body is in an unpressurized state. The amount of tension the resilient portion 52 provides is directly proportional to the amount of tension the cuff exerts on the operative limb 42 and depends on how much force the resilient portion absorbs in an extended state. While maintaining the securing strap 18 in the taut condition and the resilient portion 52 in the fully extended state, the user then wraps the securing strap 18 around the limb while pressing radially inward to secure the securing strap 18 against the engagement pad 36 on the main member 14. This secures the body 12 in a tensioned state with the desired tension force as described above.

When the resilient portion 52 is in its fully extended state and/or when the securing portion is generally taut, this indicates that a sufficient force is being applied and the securing portion should be engaged with the body 12 to secure the body 12 to the limb 42. Here, generally taut means that the body 12 is at least taut along a length of the body wrapped around the limb 42 on which the resilient portion 52 extends. Thus, in the present example, generally taut means taut from at least the proximal end portion 24 of the main member 14 and for a length of the securing strap to where the distal end portion 58 of the resilient portion 52 connects to the distal end portion 26 of the securing strap 18. Thus, any extra length of the body 12 distal from the distal end portion 58 of the resilient portion may or may not be pulled taut depending on where a user grasps the securing strap 18.

While the resilient portion 52 absorbs forces while it is extending, once the resilient portion 52 is fully extended and the securing strap 18 is taut, further pulling on the securing strap will cause those further forces to apply too much tension to the main member 14 still causing over-tightening of the body 12. Thus, the user is provided with instructions to stop pulling and secure the securing strap 18 once the slack in the securing strap 18 is removed and the securing strap is taut as already explained.

The resilient portion 52 also helps to secure the hook-loop connectors to each other by applying a slight downward (radially inward for example) force to the hook and loop fabric. This forces the hooks to engage farther into the loops reducing the chances of unintentional separation.

Since the cuff 10 will not significantly affect blood pressure in the limb 42 pressure when the cuff is deflated, the cuff 10 also helps to maintain blood pressure in the limb and air pressure in the tourniquet cuff closer to ideal values. This is desirable with tourniquet machines, such as Zimmer's A.T.S.® 3000 tourniquet system, that detect and display limb occlusion pressure (LOP) and then display a recommended tourniquet pressure (RTP) for providing a minimum amount of tourniquet pressure (including safety margins) to safely provide occlusion. When these values are not within ideal ranges, the practitioners may believe something is wrong. In fact, nothing is wrong because the tourniquet machine simply compensates for the actual LOP and RTP values that result from a tourniquet that is not applied correctly. For instance, when a tourniquet cuff is too loose, the LOP and RTP values may be higher than normal. A cuff that is applied too tight may result in LOP and RTP values that are lower than normal. Thus, the tourniquet machine will need to supply more volume of air and potentially more pressure for a cuff that is too loose and less pressure for a cuff that is too tight due to the fact that the inappropriately tight cuff is providing partial occlusion for the tourniquet machine to obtain the desired stop in blood pulse in the limb. Also, a cuff that is inappropriately applied too tight can significantly reduce the overall cuff volume which can tend to make cuff pressure regulation more difficult for electronically controlled tourniquet machines. The difficulty can be in part a control hysteresis where as the control system will oscillate around the set pressure with improper pressure amplitude. The present cuff 10, however, avoids this problem of possibly unnecessarily alarming medical personnel by significantly increasing the chances that the cuff 10 will be applied properly.

Figure 4:
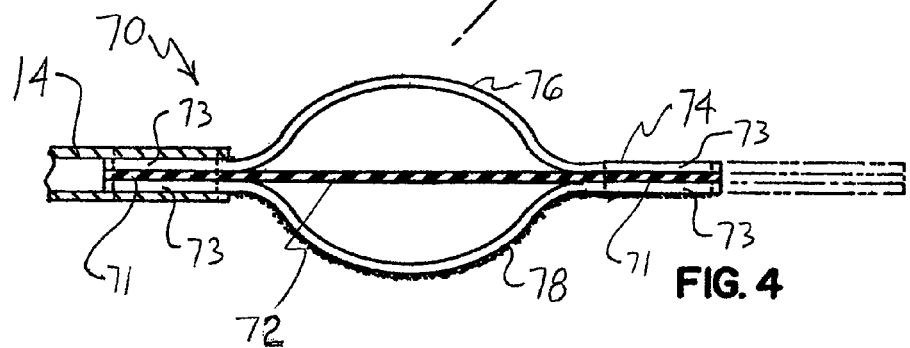
FIG. 4 is a fragmentary side, cross-sectional view showing a securing strap portion of an alternative tourniquet in accordance with the present invention.

Referring now to FIG. 4, in an alternative form, a tourniquet cuff 70 has at least one resiliently extendable portion or resilient portion 72 disposed at least partially within a securing strap 74. Features that are similar to that on tourniquet cuff 10 are otherwise numbered similarly. The securing strap 74 has outer layers 76 and 78 that at least partially or completely enclose the resilient portion 72 where the side edges (facing into and out of the paper in FIG. 4) of the layers may be connected to each other. While the outer layers 76 and 78 are flexible to provide sufficient space between them to permit the resilient portion 72 to flex, bend, and/or compress, the outer layers 76 and 78 may have a maximum extended orientation (as shown in phantom line) where the layers are pulled taut as with the securing strap 18. Opposite ends 71 of the resilient portion 72 and the corresponding ends 73 of the layers 76 and 78 maybe connected to each other by methods mentioned above for the resilient portion 16 and securing strap 18. The resilient portion 72 and the outer layers 76 and 78 are also made of materials similar to that mentioned above for the resilient portion 16 and the securing strap 18.

Figure 5:
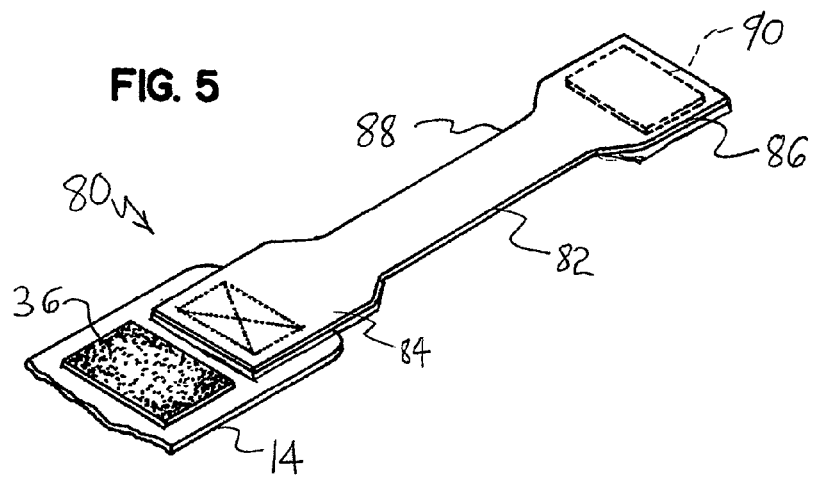
FIG. 5 is a fragmentary, front perspective view showing a securing strap portion of another alternative tourniquet cuff in accordance with the present invention.

Referring to FIG. 5, in this alternative form, a cuff 80 has a resilient portion 82 integrally formed with non-resilient end portions 84 and 86 to form a securing strap 88. The securing strap 84 may be made of a polymer that provides the resilient portion 82 with a memory for its natural length but that can be extended when pulled by a user. The non-resilient, stiffer end portions 84 and 86 are wider and thicker than the resilient portion 82 to restrict such resiliency at the end portions. For this case, the distal end portion 86 has a hook or loop pad 90 (shown in dashed line) to engage the hook or loop patch 36 on the main member 14 when the cuff 80 is wrapped around a limb. The user may be instructed to pull the securing strap 88 until the securing strap attains a visible predetermined shape such as with a predetermined extended length or a predetermined reduced width caused by the stretching of the resilient portion 82.

Figure 6:
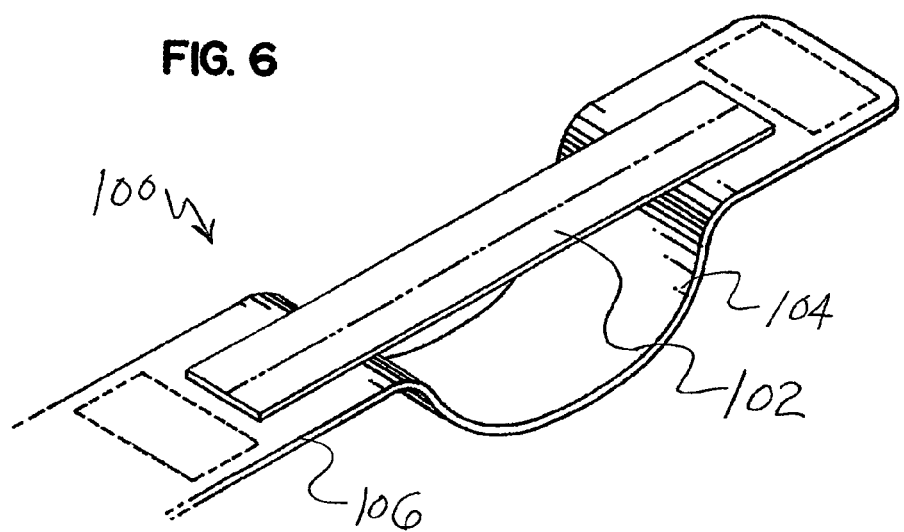
FIG. 6 is a front perspective view of yet another alternative tourniquet cuff in accordance with the present invention.

Referring to FIG. 6, in another form, a tourniquet cuff 100 does not have a securing strap, and a resilient portion 102 spans a slackened, distal portion 104 of a main body 106 of the cuff. The cuff 100 otherwise operates similarly to the cuff 10.

Figure 7:
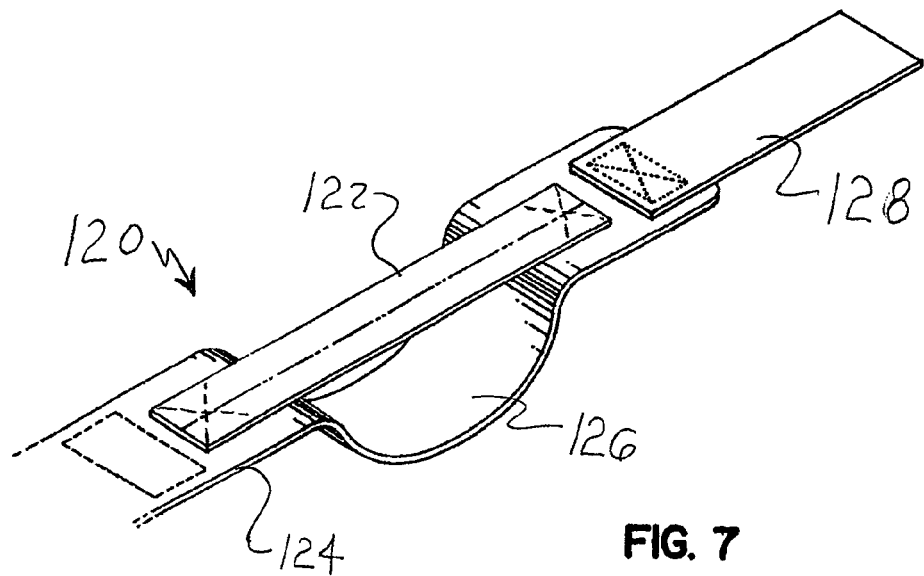
FIG. 7 is a front perspective view of a further alternative tourniquet cuff in accordance with the present invention.

Similarly, referring to FIG. 7, an alternative tourniquet cuff 120 also has a resilient portion 122 on a main body 124 of the cuff and that spans a slackened distal portion 126 of the body 124. Here, however, the cuff 120 also has a separate securing strap 128 similar to securing strap 18 but that is not connected to the resilient portion 122.

It will be appreciated that other forms of the resilient portions described herein are also contemplated such as extension springs whether in coil form or other forms as well as resilient cables, cords, or any other device that is extendable and has a memory for its original length. Of course, if any of the cuffs described herein are disposable, it will be understood that the resilient portion maybe configured so that it intentionally cannot reestablish its natural, non-extended length in order to force the user to dispose of the cuff.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tourniquet cuff, comprising:
   a body configured for being wrapped around a limb, the body having an unpressurized state and a pressurized state and having a securing portion having a first end secured to a main member of the body and a second free end releasably engageable to the body, the main member of the body including a pressurizable bladder;
   an elastic member having a first end portion secured to the body at a first location, a second end portion secured to the securing portion at a second location, and an intermediate portion extending along a front face of the securing portion between the first and second end portions that is free to elongate relative to the securing portion by pulling on the second free end of the securing portion; and
   the securing portion cooperating with the elastic member to provide an indicator that operates in response to elongation of the elastic member from a first length to a second length greater than the first length for locating where the securing portion is to engage the body in order to apply a predetermined amount of force to the limb with the body in the unpressurized state sufficient to secure the body to the limb without causing significant venous occlusion at the limb.

2. The tourniquet cuff of claim 1, wherein the elastic member has a natural bias against extension, the elastic member configured to extend against the natural bias as the securing portion is being wrapped around a limb for securement to the body.

3. The tourniquet cuff of claim 2, wherein the elastic member has a natural length and a fully extended length and the fully extended length indicates that the securing portion has been sufficiently wrapped around a limb and is to be engaged with the body to secure the body to a limb.

4. The tourniquet cuff of claim 2, wherein the body has a taut state, and wherein the elastic member is configured and disposed on the body to absorb force while the body is pulled into the taut state.

5. The tourniquet cuff of claim 4, wherein the taut state indicates that a sufficient amount of tension is applied to the body and that the second free end of the securing portion should be attached to the body.

6. The tourniquet cuff of claim 4, wherein the body has a proximal end portion for contacting the limb, wherein the taut state comprises the body being generally taut from the proximal end portion to at least the second end portion of the elastic member.

7. The tourniquet cuff of claim 2, wherein the body has a proximal end portion for being placed against the limb and an intermediate portion disposed between the proximal end portion and the securing portion, and wherein the elastic member extends from the intermediate portion to the second free end of the securing portion.

8. The tourniquet cuff of claim 1, wherein the securing portion includes a securing strap extending generally along the elastic member when pulled taut.

9. The tourniquet cuff of claim 8, wherein the elastic member is stretched to a predetermined extension to indicate that the cuff is sufficiently wrapped about the limb.

10. The tourniquet cuff of claim 8, wherein the elastic member is elongated to the second length when the securing strap is generally taut from the main member to the second end portion of the elastic member.

11. The tourniquet cuff of claim 8, wherein the intermediate portion extends generally along the securing strap when the securing strap is in a taut state and is free to move away from the securing strap when the securing strap is in a slackened state.

12. The tourniquet cuff of claim 8, wherein the elastic member is disposed at least partially within the securing strap.

13. The tourniquet cuff of claim 8, wherein the elastic member comprises a plurality of generally parallel extending resiliently extendable members.

14. The tourniquet cuff of claim 8, wherein the elastic member is configured to be stretched against a natural bias of the elastic member as the securing strap is pulled generally taut from a slackened state to indicate the predetermined amount of force is applied to the limb.

15. A tourniquet cuff comprising:
a main member configured for being wrapped around a limb and having an unpressurized state and a pressurized state, the main member including a pressurizable fluid tight bladder;
a securing portion including a securing strap having an attachment end portion connected to the main member and a free end portion being releasably engageable to the main member; and
an indicator for indicating that the free end portion has been moved around the limb a sufficient distance for the main member to apply a predetermined amount of force to a limb when the main member is in the unpressurized state for snugly holding the main member on the limb without causing significant venous occlusion at the limb;
wherein the indicator includes at least one resilient member, the securing strap extending between a first end portion of the at least one resilient member to a second end portion of the at least one resilient member, the at least one resilient member being expandable against a natural bias from a first length to a second length greater than the first length as the securing strap is drawn from a slackened state to a taut state without lengthening the securing strap between the first and second end portions of the securing strap; and
wherein the first end portion of the at least one resilient member and the second end portion of the at least one resilient member are directly connected to a front face of the securing strap.

16. The tourniquet cuff of claim 15, wherein the securing strap is configured such that drawing the securing strap to the taut state is indicative that the predetermined amount of force is applied to the limb.

17. The tourniquet cuff of claim 15, wherein the first end portion is connected to the main member, the second end portion is connected to the securing strap, and an intermediate portion between the first and second end portions is unconnected to the securing strap.

18. The tourniquet cuff of claim 15 wherein the at least one resilient member comprises a plurality of generally parallel extending resilient members.

19. A tourniquet cuff comprising:
a body configured to be wrapped around a limb and having an unpressurized state and a pressurized state, the body including a main member and a securing portion having a first end secured to the main member and a second free end releasably engageable to the main member when wrapped around the limb, the main member including a bladder configured to put the body in a pressurized state when the bladder is pressurized;
the securing portion including a securing strap; and
a resilient member including a first end portion and a second end portion, the first end portion of the resilient member secured to a first end portion of a front face of the securing strap and the resilient member extends along the front face to a position where the second end portion of the resilient member is directly secured to a second end portion of the front face of the securing strap, the resilient member having a first length between the first and second end portions of the resilient member in a relaxed state and a second length greater than the first length between the first and second end portions of the resilient member in a tensioned state, the resilient member configured to be drawn into tension from the first length to the second length without lengthening the securing strap between the first and second end portions of the securing strap;
wherein when the second free end of the securing portion is wrapped around the limb and releasably engaged to the main member while the resilient member is tensioned at the second length, the body applies a force to the limb when the body is in the unpressurized state to secure the body to the limb without causing significant venous occlusion at the limb.

20. The tourniquet cuff of claim 19, wherein the securing strap extends from the main member along a first side of the resilient member to the second free end of the securing portion;
wherein the securing strap is in a slackened state when the resilient member is at the first length and the securing strap is in a taut state when the resilient member is at the second length.

21. A tourniquet cuff comprising:
a body configured to be wrapped around a limb and having an unpressurized state and a pressurized state, the body including a main member and a securing portion having a first end secured to the main member and a second free end releasably engageable to the main member when wrapped around the limb, the main member including a bladder and one or more ports configured to receive air to pressurize the bladder;
a resilient member configured to be drawn into tension from a first length to a second predetermined length greater than the first length;
wherein when the second free end of the securing portion is wrapped around the limb and releasably engaged to the main member while the resilient member is tensioned at the second predetermined length, the body applies a predetermined amount of force to the limb when the body is in the unpressurized state to secure the body to the limb without causing significant venous occlusion at the limb;
wherein the securing portion includes a securing strap extending from the main member along a first side of the resilient member to the second free end of the securing portion;
wherein the securing strap is in a slackened state when the resilient member is at the first length and the securing strap is in a taut state when the resilient member is at the second predetermined length;
wherein the resilient member includes a first end portion connected to the securing strap proximate the first end of the securing portion, a second end portion connected to the securing strap proximate the second free end of the securing portion, and an intermediate portion between the first end portion and the second end portion of the resilient member;

wherein the intermediate portion of the resilient member generally extends along the securing strap such the first side of the intermediate portion of the resilient member contacts the securing strap when the resilient member is tensioned to the second predetermined length; and wherein the intermediate portion of the resilient member is free to move away from the securing strap such that the first side of the intermediate portion of the resilient member moves out of contact with the securing strap when the resilient member is at the first length.

\* \* \* \* \*